United States Patent
Kuisma

(10) Patent No.: US 11,617,542 B2
(45) Date of Patent: Apr. 4, 2023

(54) ELECTRICAL INTERCONNECTION FOR A CATHETER

(71) Applicant: MURATA MANUFACTURING CO., LTD., Nagaokakyo (JP)

(72) Inventor: Heikki Kuisma, Helsinki (FI)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 987 days.

(21) Appl. No.: 16/136,481

(22) Filed: Sep. 20, 2018

(65) Prior Publication Data
US 2019/0133527 A1    May 9, 2019

(30) Foreign Application Priority Data

Nov. 8, 2017 (FI) ..................................... 20175998

(51) Int. Cl.
*A61B 5/00* (2006.01)
*H05K 1/18* (2006.01)
(Continued)

(52) U.S. Cl.
CPC .......... *A61B 5/6852* (2013.01); *A61B 5/0215* (2013.01); *A61M 25/0012* (2013.01);
(Continued)

(58) Field of Classification Search
CPC . A61B 5/6852; A61B 5/0215; A61B 2562/12; A61B 5/02007; A61B 5/02158;
(Continued)

(56) References Cited

U.S. PATENT DOCUMENTS

| 4,274,423 A | * | 6/1981 | Mizuno ................ A61B 5/0215 600/488 |
| 4,815,472 A | | 3/1989 | Wise et al. |

(Continued)

FOREIGN PATENT DOCUMENTS

| EP | 1 671 669 A1 | 6/2006 |
| WO | WO 2011/005165 A1 | 1/2011 |
| WO | WO 2016/171597 A1 | 10/2016 |

OTHER PUBLICATIONS

Kärkkäinen, Anu, et al. "New MEMS pressure sensor element and concept for coronary catheter." Procedia Engineering 168 (2016): 76-79 (Kärkkäinen) (Year: 2016).*
(Continued)

*Primary Examiner* — Christian Jang
*Assistant Examiner* — Mitchell E Alter
(74) *Attorney, Agent, or Firm* — Squire Patton Boggs (US) LLP

(57) ABSTRACT

The present invention relates to an elongated catheter comprising a tubular section with a side wall with essentially annular cross-section defined by an outer surface and an inner surface of the tubular section. In the outer surface of the tubular section, there is at least one longitudinal installation recess extending over a first predefined distance over the longitudinal dimension of the catheter. A flexible circuit board is wrapped around the tubular section. Electrical wiring is disposed on the outer surface of the tubular section. At least one electronic device is assembled on the flexible circuit board and disposed within the at least one longitudinal installation recess. The at least one electronic device is interconnected via the flexible circuit board with the electrical wiring.

22 Claims, 8 Drawing Sheets

(51) Int. Cl.
*H05K 5/06* (2006.01)
*H05K 3/28* (2006.01)
*A61M 25/00* (2006.01)
*A61B 5/0215* (2006.01)

(52) U.S. Cl.
CPC ............. *H05K 1/189* (2013.01); *H05K 3/284* (2013.01); *H05K 5/065* (2013.01); *A61B 2562/12* (2013.01); *H05K 2201/056* (2013.01); *H05K 2201/10151* (2013.01); *H05K 2201/10674* (2013.01)

(58) Field of Classification Search
CPC ... A61M 25/0012; H05K 1/189; H05K 3/284; H05K 5/065; H05K 2201/056; H05K 2201/10151; H05K 2201/10674
USPC .......................................................... 600/486
See application file for complete search history.

(56) References Cited

U.S. PATENT DOCUMENTS

| 5,226,423 | A | 7/1993 | Tenerz et al. | |
|---|---|---|---|---|
| 6,283,921 | B1 * | 9/2001 | Nix | A61B 8/12 600/466 |
| 2005/0187487 | A1 * | 8/2005 | Azizkhan | A61B 5/0215 600/561 |
| 2007/0219551 | A1 * | 9/2007 | Honour | A61B 5/6852 606/41 |
| 2012/0172731 | A1 * | 7/2012 | Smith | A61B 5/0215 600/486 |
| 2013/0225962 | A1 * | 8/2013 | Saleh | A61B 5/065 600/373 |
| 2013/0237864 | A1 | 9/2013 | Mazar et al. | |
| 2015/0196210 | A1 | 7/2015 | McCaffrey et al. | |

OTHER PUBLICATIONS

Dekker, Ronald, et al. "Living Chips and Chips for the living." 2012 IEEE Bipolar/BiCMOS Circuits and Technology Meeting (BCTM). IEEE, 2012 (Dekker) (Year: 2012).*
Tempo Automation (Year: NA).*
Finnish Search Report dated Jun. 1, 2018 corresponding to Finnish Patent Application No. 20175998.
F. Stam et al., "Integration of a Capacitive Pressure Sensing System into the Outer Catheter Wall for Coronary Artery FFR Measurements," In: Bio-MEMS and Medical Microdevices III, SPIE Proceedings, Society of Photo-Optical Instrumentation Engineers (SPIE), May 31, 2017.

* cited by examiner

ELECTRICAL INTERCONNECTION FOR A CATHETER

FIELD

The present invention relates to a catheter configured to be inserted in a blood vessel. More particularly, the present invention relates to mechanical and electrical assembly of a catheter.

BACKGROUND

Fractional flow reserve measurement is an established method for determining the extent of a stenosis in cardiac arteries. A pulsating pressure is measured on a proximal side and on a distal side of a stenosis, and the ratio between the averages of the two pressure readings is used as an indication of the degree of stenosis and the need for treatment.

For measuring the pressure within a cardiac artery, a catheter is inserted to a major artery of the patient at the groin, neck or wrist, and the catheter is navigated through the blood vessels to the intended destination to be investigated.

Guide wires are typically tiny and equipped with a flexible tip which facilitates navigation in blood vessels to reach a lesion or vessel segment. Once the tip arrives at its destination, it acts as a guide, which a larger and typically stiffer catheter can rapidly follow for easier delivery to the measurement and/or treatment site. A guide wire may also serve as a visual guide to the operating personnel, as it is typically made of material which is visible in X-ray imager. Thus, the position of the guide wire can be seen at all times. A fast exchange catheter is a catheter type known in the art in which a guide wire is only disposed at the distal end of the catheter.

DESCRIPTION OF THE RELATED ART

Portions of the invention were disclosed in a publication entitled "Integration of a capacitive pressure sensing system into the outer catheter wall for coronary artery FFR measurements", published on 2017 May 31 in Bio-MEMS and Medical Microdevices III, SPIE Proceedings, which is before the effective filing date of the subject application. However, this publication was authored by Heikki Kuisma, who is inventor of the subject matter of this application, and Frank Stam, Geng Gao, Jaakko Saarilahti, David Gomes Martins, Anu Kärkkäinen, Brendan Marrinan and Sebastian Pintal, who are not inventors. Pursuant to AIA 35 U.S.C. Section 102(b)(1), this disclosure is not prior art under 35 USC section 102 since it was made 1 year or less before the effective filing date of this application, and the disclosure was made the inventor or by another who had obtained the subject matter disclosed directly or indirectly from the inventor.

U.S. Pat. No. 5,226,423 discloses a medical device integrated in a guide wire with a pressure sensor for measuring pressure in stenotic vessels.

U.S. Pat. No. 4,815,472 discloses a multipoint pressure-sensing catheter for measuring pressure in cardiac arteries. This catheter is not configured to utilize a guide wire.

US patent application 2013/0237864 discloses an elongate intravascular guide wire in which where electronics are added to the guide wire as a thicker bulging section.

SUMMARY

An object is to provide a method and apparatus so as to solve the problem of assembling electronic devices on a catheter configured to carry the electronic devices into a blood vessel. The objects of the present invention are achieved with an apparatus according to the claim 1 and a method according to the claim 15.

The preferred embodiments of the invention are disclosed in the dependent claims.

The present invention is based on the idea of disposing at least one electronic device within the volume of a side wall of a tubular section of a catheter, and to provide electrical connections for the at least one electrical device with a flexible circuit board wrapped around the tubular section of the catheter.

The present invention has the advantage that use of the flexible circuit board allows fast, simple and reliable assembly of the electronic devices on the catheter, but does not significantly increase the diameter of the catheter nor cause the catheter to become excessively rigid. Assembling the electronic devices into the side walls of the catheter and coupling them electrically utilizing the outer periphery of the catheter body enables maintaining tubular form of the catheter with a lumen also at the location with electronic devices. The lumen facilitates use of guide wire for agile navigation. The cardiac catheter is typically 0.66 mm in diameter and thus the peripheral length is 2.07 mm. Utilization of the periphery of the catheter body as the assembly area for electronics and interconnections maximizes the available area for the electronics and the interconnections, thus enabling both increased functionality and complexity of the electronic system and allowing use of relaxed design rules for the interconnections, e.g. having 0.1 mm track and spacing width instead of 0.025 mm, which would be typically required without wrapping the flexible circuit. The large peripheral length also enables easy assembly of electrical wires to the flexible circuit board by soldering or with an electrically conductive adhesive.

According to a first aspect, an elongated catheter comprising a tubular section with a side wall with essentially annular cross-section defined by an outer surface and an inner surface of the tubular section is provided. At least one longitudinal installation recess is disposed in the outer surface of the tubular section. A flexible circuit board is wrapped around the tubular section. Electrical wiring is disposed on the outer surface of the tubular section. At least one electronic device is assembled on the flexible circuit board and disposed within the at least one longitudinal installation recess. The at least one electronic device is interconnected via the flexible circuit board with the electrical wiring.

According to a second aspect, the at least one electronic device comprises at least one first electronic device and at least one second electronic device. The at least one first electronic device and the at least one second electronic device are assembled on the flexible circuit board and disposed within at least one longitudinal installation recess. The at least one first electronic device is interconnected via the flexible circuit board with the electrical wiring and the at least one second electronic device is interconnected via the flexible circuit board with the first electronic device.

According to a third aspect, at least predefined portions of the flexible circuit board wrapped on the tubular section essentially encircle the tubular section of the catheter.

According to a fourth aspect, the at least one installation recess extends a first predefined distance over the longitudinal dimension of the catheter and the flexible circuit board extends a second predefined distance along the longitudinal dimension of the catheter. The second predefined distance is greater than the first predefined distance, and the flexible circuit board covers at least a majority of the at least one installation recess on the outer surface of the tubular section.

According to a fifth aspect, an essentially circular cross-section of the wrapped flexible circuit board comprises one or more essentially circular segments and at least one chordal segment at the portion of the cross-section of the wrapped flexible circuit board at which the at least one electronic device is assembled on the flexible circuit board.

According to a sixth aspect, the depth of the at least one installation recess is less than the distance between the outer surface and the inner surface of the tubular section, but more than the height of the at least one electronic device within the installation recess.

According to a seventh aspect, the cross section of the at least one installation recess is any one of a quadrangle crossing the outer surface of the tubular section so that two opposite sides of the quadrangle cross the outer surface of the tubular section, and a minor chordal segment removed from the outer surface of the tubular section.

According to an eighth aspect, the at least one electronic device is of flip chip type.

According to a ninth aspect, a wrapping layer configured to hold the flexible circuit board in place and to confirm the outer periphery of the catheter is disposed around the catheter at least over the second distance along the longitudinal dimension of the catheter.

According to a tenth aspect, the wrapping layer comprises adhesive heat shrinkable tubing.

According to an eleventh aspect, the electrical wiring disposed on the outer surface of the tubular section is configured to lead at least one of electrical power and a control signal into at least one of the electronic devices and to lead electrical signals out of at least one of the electronic devices.

According to a twelfth aspect, a protective filling is applied into the installation recess in which the at least one electronic device is disposed. The protective filling configured to surround the at least one electronic device on all sides and to prevent direct contact of bodily fluids with the at least one electronic device.

According to a thirteenth aspect, the flexible circuit board further comprises at least one hole at least partially collocated with the installation recess, the at least one hole configured to enable application of protective filling into the installation recess and/or to enable evacuation of air from the installation recess during application of the protective filling.

According to a fourteenth aspect, the flexible circuit board further comprises at least one elongated cut-out collocated with at least one electronic device. The at least one elongated cut-out is configured to prevent changes in the internal pressure of the protective filling within the underlying installation recess due to temperature changes by allowing the protective filling to expand and contract.

According to a first method aspect, a method for manufacturing an elongated catheter is provided. The catheter comprises a tubular section with a side wall with essentially annular cross-section defined by an outer surface and an inner surface of the tubular section. The method comprises assembling at least one electronic device on a flexible circuit board. The method comprises wrapping the flexible circuit board around the tubular section of the catheter and disposing the at least one first electronic device within at least one longitudinal installation recess in the outer surface of the tubular section. The at least one installation recess extends over a first predefined distance over the longitudinal dimension of the catheter. The method comprises interconnecting the at least one first electronic device with electrical wiring disposed on the outer surface of the tubular section via the flexible circuit board.

According to a second method aspect, the at least one electronic device comprises at least one first electronic device and at least one second electronic device, and the method comprises assembling the at least one first electronic device and the at least one second electronic device on the flexible circuit board and disposed within the at least one longitudinal installation recess, interconnecting the at least one first electronic device is interconnected via the flexible circuit board with the electrical wiring and interconnecting the at least one second electronic device via the flexible circuit board with the first electronic device.

According to a third method aspect, wrapping causes at least predefined portions of the flexible circuit board to essentially encircle the tubular section of the catheter.

According to a fourth method aspect, the at least one installation recess extends a first predefined distance over the longitudinal dimension of the catheter, the flexible circuit board extends a second predefined distance along the longitudinal dimension of the catheter, and the second predefined distance is greater than the first predefined distance. The method comprises disposing the flexible circuit board so that it covers at least a majority of the at least one installation recess on the outer surface of the tubular section.

According to a fifth method aspect, the method further comprises disposing a wrapping layer configured to hold the flexible circuit board in place and to confirm the outer periphery of the catheter around the catheter at least over a second distance along the longitudinal dimension of the catheter.

According to a sixth method aspect, the method further comprises applying a protective filling into the installation recess in which the at least one electronic device is disposed. The protective filling is configured to surround the at least one electronic device on all sides and to prevent direct contact of bodily fluids with the at least one electronic device.

According to a seventh method aspect, the method further comprises manufacturing in the flexible circuit board at least one hole configured to be at least partially collocated with the installation recess. The at least one hole is configured to enable application of protective filling into the installation recess and/or to enable evacuation of air from the installation recess during application of the protective filling.

According to an eighth method aspect, the method further comprises manufacturing in the flexible circuit board at least one elongated cut-out configured to be collocated with at least one electronic device. The at least one elongated cut-out is configured to prevent changes in the internal pressure of the protective filling within the underlying installation recess due to temperature changes by allowing the protective filling to expand and contract.

BRIEF DESCRIPTION OF THE DRAWINGS

In the following the invention will be described in greater detail, in connection with preferred embodiments, with reference to the attached drawings, in which.

DETAILED DESCRIPTION

The term distal end refers to the end of an elongate catheter structure that is configured to be inserted into a blood vessel, while the term proximal end refers to the end of the catheter that remains outside of the body of the patient. The term distal portion refers to a portion of the catheter starting from the distal end and the term proximal portion refers to any portion that resides between the distal portion and the proximal end of the elongate catheter structure.

Terms long and longitudinal refer to a direction aligned with the longitudinal dimension of the elongate catheter.

The term annular cross-section in this context refers to a region in plane between two circumferential perimeters, each with a circular or oval shape, a smaller perimeter nested inside a larger perimeter. In a tubular element, the larger perimeter is formed by an outer surface of the tubular element, the smaller perimeter by an inner surface of the tubular element. The term side wall refers to the layer of material between the outer surface and the inner surface of the tubular element. In case of two circular perimeter shapes, the circles may be concentric or eccentric. Thus, the term essentially annular cross-section refers herein to any one of a concentric annular or an eccentric annular cross-section. The term essentially annular cross section further refers herein to tubular forms where the outer perimeter may include small deviations from the circular or oval shape, for example a chord formed of an essentially straight line connecting two points on the otherwise circular form. Likewise, the term essentially circular refers herein to a circular form that may include small deviations from the circular shape, for example a chord formed of an essentially straight line connecting two points on the otherwise circular form.

FIGS. 1a to 1h illustrate a catheter assembly according to a first exemplary embodiment.

Figure 1A:
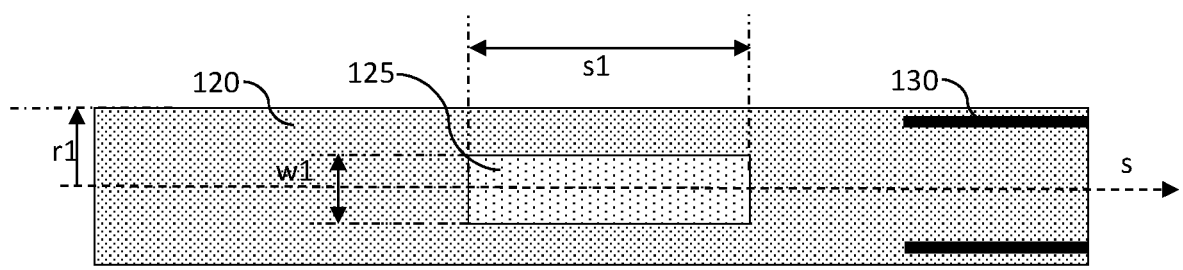
FIGS. 1a to 1h illustrate a catheter assembly according to a first embodiment.

FIG. 1a illustrates a lateral, longitudinal view of a portion of a catheter body 120. The portion is preferably tubular, comprising a lumen (not shown) traversing through the catheter in the longitudinal direction s. The term catheter body 120 refers to an elongate piece of flexible material. A typical cardiac catheter body 120 has a diameter of 0.66 mm, but in some occasions, the diameter may be up to 1 mm. Side wall of the catheter body 120 defines the lumen. The catheter body 120 is preferably annular, and the cross-sections of both the outer surface of the catheter body 120 and the lumen are preferably essentially circular. The essentially circular cross-section of the outer surface of the catheter body 120 is preferred because the catheter is configured to be inserted in blood vessels with circular form. The essentially circular cross-section of the lumen is preferred as it facilitates ease of insertion of a typically circular guide wire into the lumen. Diameter of the circular lumen may be for example 0.33 mm. The annular catheter body 120 has a radius r1, and its diameter 2*r1 may be for example 0.66 mm. Alternatively, the cross-section of the catheter body may also be for example elliptic. A catheter body 120 having an essentially annular cross-section may also have one or more flat portions.

Within the side wall of the catheter body 120, an oblong installation recess 125 is formed. The installation recess 125 extends in the longitudinal direction s of the catheter body 120 a first predetermined length s1, which may vary between 0.5 mm and 10 mm. Width w1 of the installation recess 125 is preferably less than the diameter (2*r1) of the catheter body 120. The width w1 may vary for example between 0.2 mm and 0.4 mm. The installation recess 125 is shallow compared to the thickness of the side wall into which it is formed, so that the installation recess 125 does not penetrate through the side wall. Thus, the installation recess 125 does not reach the lumen. Thickness of the side wall may be measured radially, and it does not have to be equal on all sides of the catheter body 120. The recess depth may vary for example between 0.1 mm and 0.2 mm. Electrical wiring 130 may be disposed on the outer surface of the side wall of the catheter body 120. The electrical wiring 130 may comprise one or more wires. Thickness or diameter of wires of the electrical wiring 130 may be for example between 20 and 50 μm. The electrical wiring 130 is configured to carry electrical power and control signals from the proximal end of the catheter to one or more electronic devices carried by the catheter, and to carry electrical signals from the one or more electronic devices towards the proximal end of the catheter. The installation recess 125 may be at least partially filled with protective filling as illustrated with light pattern fill of the installation recess 125. The electrical wiring 130 is preferably not disposed at the section(s) of the side wall with the one or more installation recesses 125.

Figure 1B:
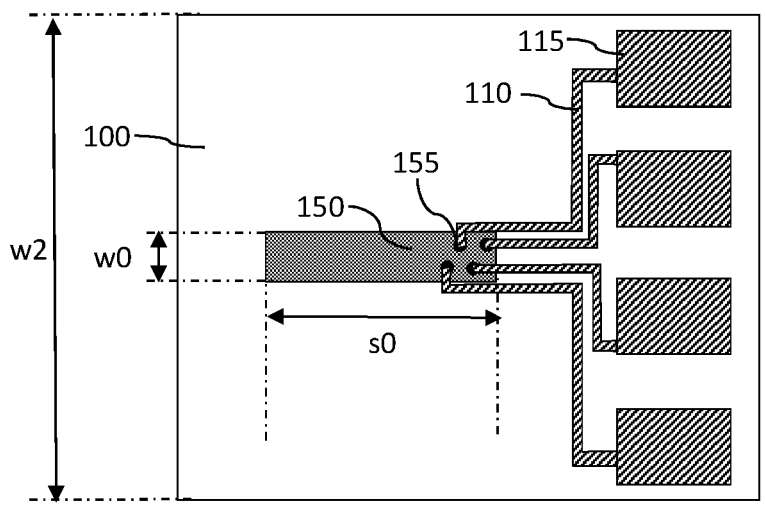

FIG. 1b illustrates a flexible circuit board 100 with wiring 110. The flexible circuit board may be made of any suitable flexible circuit board material known in the art. For example, plastic substrate such as polyimide, polyether ether ketone (PEEK) or polyester may be utilized. The wiring 110 may be disposed on the flexible circuit board for example by laminating, printing, ink jetting or with photolithographic methods known in the art. The flexible circuit board 100 may have a thickness between 10 and 50 μm.

An electronic device 150 is assembled on the flexible circuit board 100, so that chip pads of the electronic device 150 are coupled through contacts 155 to the wiring 110 of the flexible circuit board 150. The wiring 110 may comprise one or more contact pads 115 coupled to the wiring 110. In the disclosed embodiment, four contact pads 115 are provided. The electronic device 150 may be for example flip chip type. Contacts 155 of a flip chip type device comprise solder bumps, which may be soldered with the wiring 110. Other, non-limiting examples of known types of contacts 155 for flip chip devices are gold stud bumps and copper pillars.

Figure 1C:
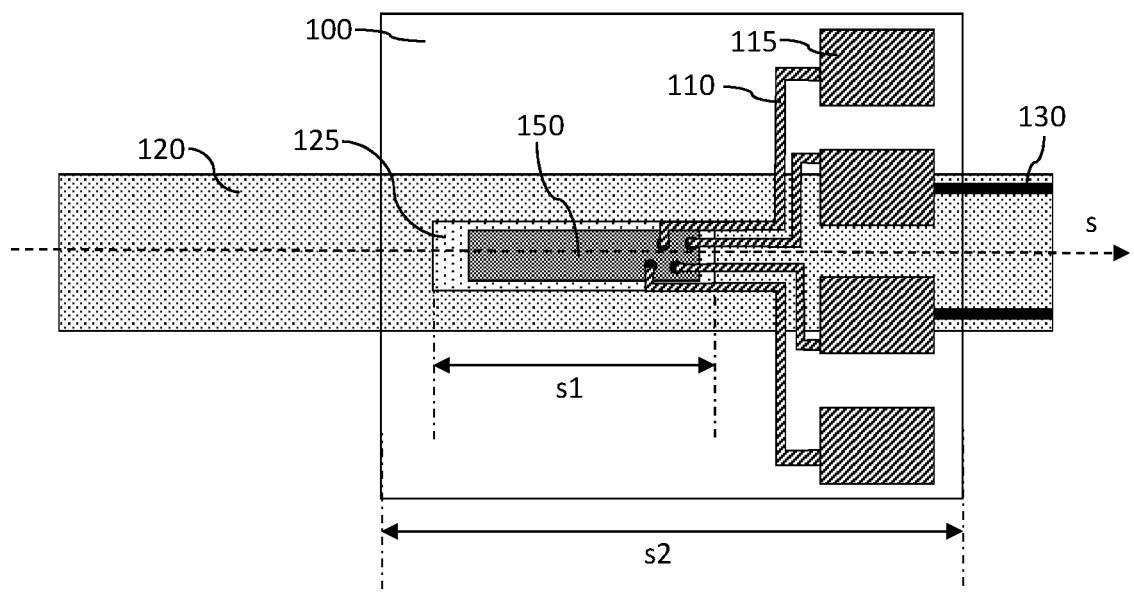

The FIG. 1c illustrates placement of the flexible circuit board 100 with the assembled electronic device 150 on the catheter body 120. The electronic device 150 is disposed in its entirety within the installation recess 150. The flexible circuit board extends along the longitudinal direction s over a second distance s2, which is greater than the first distance, so that the installation recess 125 may be entirely covered by the flexible circuit board 100. The flexible circuit board extends preferably over a distance between at least one electronic device 150 and ends of the electrical wiring 130 so that these may be interconnected via wiring 110 of the flexible circuit board. During the assembly, the remaining space within the installation recess 125 not occupied with the electronic device 150 may be filled with protective filling configured to protect the electronic device from contact with for example bodily fluids when in use. Alternatively, or in addition, a layer of protective filling may be applied on the electronic device 150 prior to disposing the electronic device 150 into the installation recess 125. The layer of protective filling is configured to protect the electronic device 150 from contacts with the bodily fluids. The protective filling may also be applied in two phases, first applying a layer on the electronic device and then filling the remaining volume of the installation recess 125 after disposing the electronic device 150 into the installation recess.

The electronic device 150 disposed in the installation recess 125 is preferably protected with protective filling or coating, as illustrated with the light pattern fill in the installation recess 125. The protective filling preferably surrounds the electronic device at all sides. Even the contacts 155 of the electronic device may be surrounded by the protective filling except at the location in which the contacts are coupled with the flexible circuit board.

Contact pads 115 of the flexible circuit board are disposed on the catheter body side wall so that they eventually become collocated with the electrical wiring 130. In order to facilitate a galvanic contact, at least part of the wiring 110 and the contact pads 115 are disposed on the surface of the flexible circuit board 100 facing the catheter body 120. For ensuring proper electrical contact between the contact pads 115 and the electrical wiring, contact pads may be mechanically and electrically coupled to the electrical wiring 130 for example by soldering or with electrically conductive adhesive. In this example, the four contact pads 115 are configured to be coupled to four different wires of the electrical wiring 130. Two of these wires are visible in the figure, but two remain invisible in the figures as they are located behind the catheter body. The number of contact pads 115 and wires in the electrical wiring 130 may vary according to the application. Preferably, there is a plurality of wires and contact pads 115.

While the electronic device 150 is oblong, the installation recess 125 is preferably also oblong so that the electronic device 150 fits nicely within the installation recess 125. Width w1 of the installation recess 125 is preferably greater than the width w0 of the electronic device 150. Length s1 of the installation recess 125 is preferably greater than the length s0 of the electronic device 150.

Figure 1D:
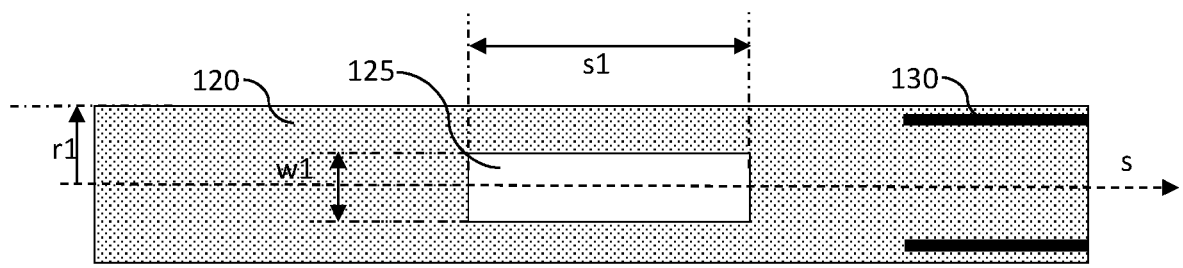
Figure 1E:
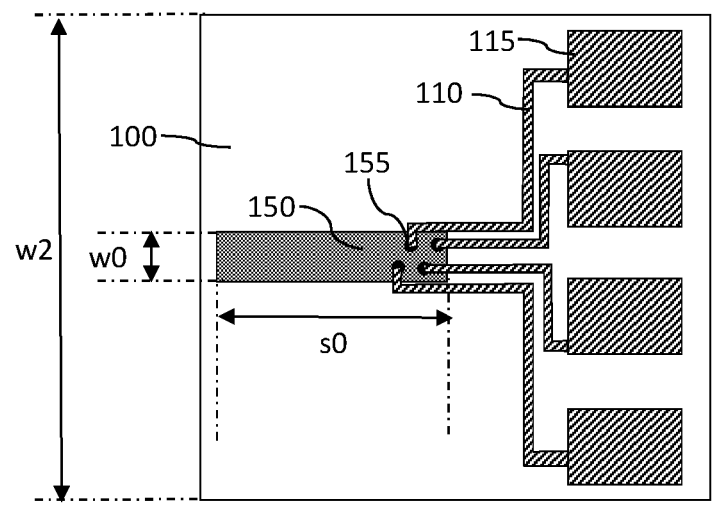
Figure 1F:
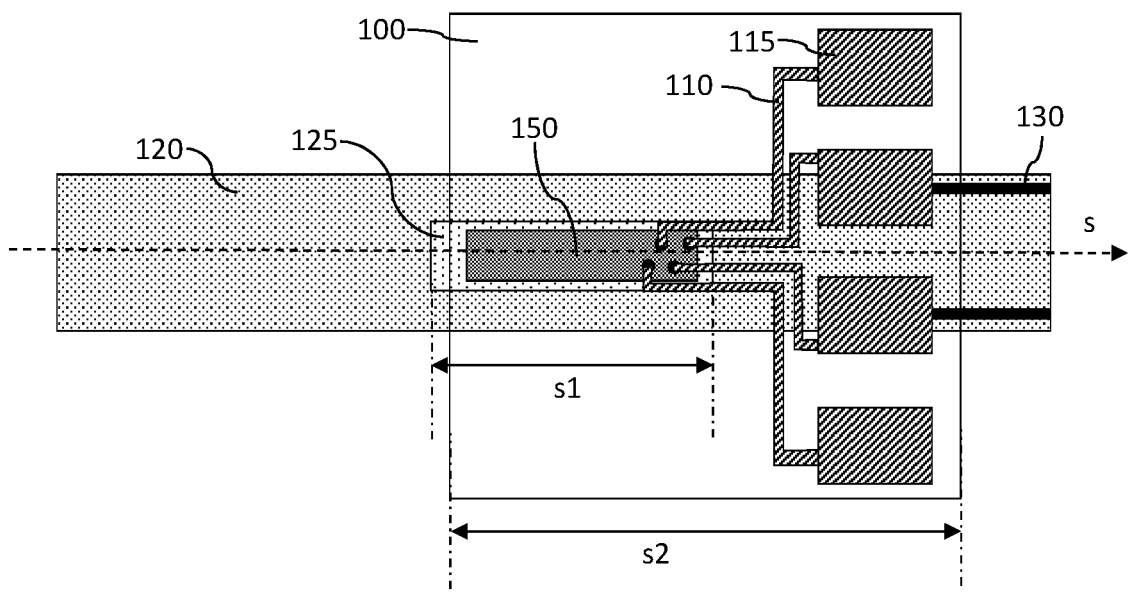

FIGS. 1d to 1f illustrate a variation of the first embodiment, in which the length s2 of the flexible circuit board is smaller than that illustrated in the FIGS. 1a to 1c. The flexible circuit board 100 in the FIG. 1e does not cover the installation recess 125 in its entirety, but a minor portion of the installation recess 125 remains uncovered. Majority of the installation recess 125 is, however, preferably covered by the flexible circuit board 100. The installation recess may be empty before assembling the flexible circuit board 100, or a limited amount of protective filling may be applied into the installation recess 125 before the assembly to ensure that the volume of the installation recess 125 under the electrical device 150 becomes properly filled. The portion of the installation recess 125 not covered by the flexible circuit board may be utilized for applying the protective filling into the installation recess 125 configured to protect the electronic device from contact with for example bodily fluids when in use. This is illustrated by adding the pattern fill representing the protective filling in the installation recess 125 only in the phase illustrated by the FIG. 1f.

As understood by a skilled person, the variation disclosed in the FIGS. 1e to 1f may be applied with any of the embodiments disclosed in this application.

Figure 1G:
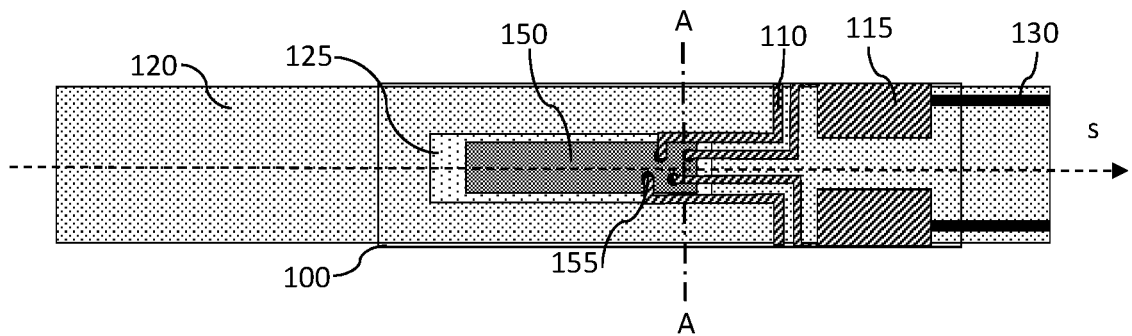
Figure 1H:
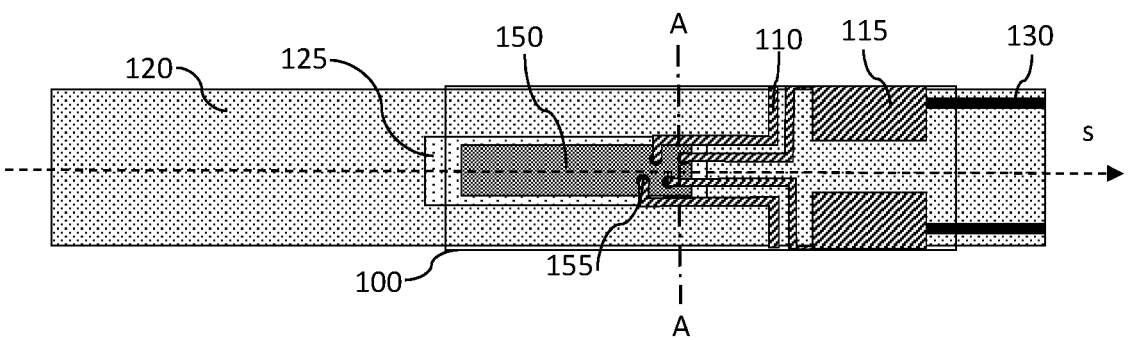

FIGS. 1g and 1h illustrate the result of wrapping of the flexible circuit board 100 around the catheter body 120. The flexible circuit board 100 now encircles the catheter body side walls and the installation recess 125 with the electronic device 150 in it, thus forming an essentially circular form. For facilitating encircling, the width w2 of the flexible circuit board 100 is preferably equal or slightly greater than the circumference $2\pi \ast r1$ of the catheter body 120, taking into account the effect of thickness of the flexible circuit board 100. Any of solder bumps, metal coated polymer bumps, gold stud bumps, copper pillars or any similar known protruding contact elements that provide coupling and a stand-off between a semiconductor die acting as the electronic device 150 and the flexible circuit board 100 may act as contacts 155 between chip pads of the electronic device 150 and the wiring 110. The wiring 110 on the flexible circuit board 100 provides electrical connections to the electronic device 150. The contact pads 115 couple electrical power and signals with the electrical wiring 130 provided at the side wall of the catheter body 120.

Figure 2:
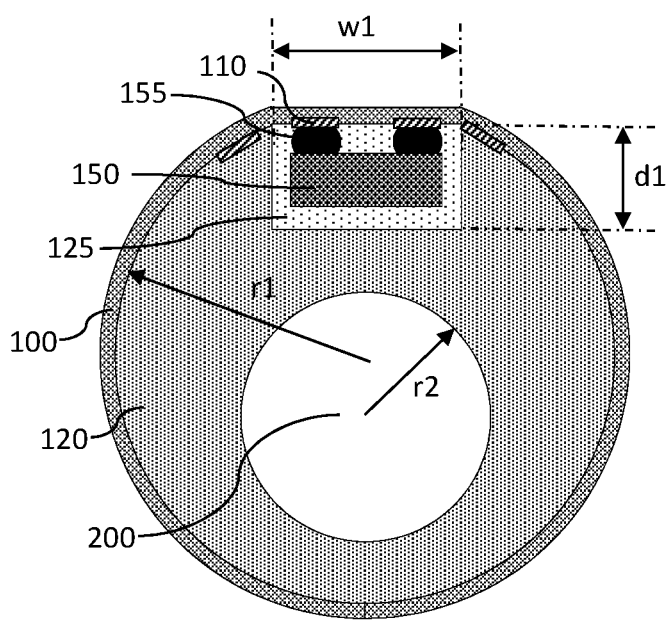
FIG. 2 illustrates cross-section of a catheter.

FIG. 2 illustrates a cross-section A-A of the tubular section of the catheter of the first embodiment illustrated in the FIGS. 1g and 1h. The essentially circular lumen 200 with a radius or r2 is disposed within the side walls of the catheter body 120. The cross-section may be characterized as essentially annular, except for the installation recess. The catheter body has a radius r1. In this embodiment, geometrical centers of the catheter body 120 and the lumen 200 are not collocated. Such eccentric placement of the lumen 200 enables varying the side wall thickness so that the side wall may be greater on one side of the tubular portion of the catheter body 120. This thicker side wall portion may be utilized for disposal of the installation recess 125. The flexible circuit board 100 is wrapped around the catheter body 120 so that the catheter body 120 becomes essentially encircled by the flexible circuit board.

The installation recess 125 is disposed at the outer surface of the side wall of the catheter body 120 so that the recess opens to the periphery of the catheter body 120. In the first embodiment, the cross-section of the installation recess 125 may be characterized as a quadrangle crossing the side wall so that two opposite sides of the quadrangle cross the outer surface of the side wall. The sides may be orthogonal, as in this example, so that the quadrangle may be characterized as a rectangle, or they may be oblique so that the quadrangle may be characterized as a trapezoid. The width of the installation recess is w1 and the depth of the installation recess is d1. The electronic device 150 coupled to the flexible circuit board 100 is disposed within the installation recess 125 in its entirety. The electronic device 150 is preferably of flip chip type known in the art. In a flip chip electronic device, contacts 155 for electrically coupling the device are provided via solder bumps or equivalent disposed directly at the chip pads of a semiconductor chip. Contacts 155 are coupled with the wiring 110 of the flexible circuit board 100. A flip chip type electronic device 150 is preferred due to its small size, as no separate, bulky semiconductor package is required. For protecting the electronic device 150 from for example bodily fluids, protective filling may be applied to enclose the electronic device 150 disposed in the installation recess 125. For example, silicone gel may be used for protective filling. The protective filling may be applied before or after assembling the electronic device 150 in the installation recess 125.

The resulting cross-section of the catheter with the flexible circuit board 100 assembled is essentially annular, but the portion with the electronic device 150 installed, the outline of the cross-section is defined by a chord, in other hands an essentially straight line connecting two points on the otherwise circular form. Thus, there is flat portion in the flexible circuit board 100. The flat portion of the wrapped flexible circuit board 100 facilitates stability of the contact between the contacts 155 and the wiring 110 on the flexible circuit board. The flat portion may extend in the longitudinal direction s at least over the entire length s1 of the installation recess 125. In such case, the flat portion may be oblong, with an area approximately equal to that of the installation recess 125. Alternatively, the flat portion may only appear in the immediate vicinity of the contacts 155.

FIG. 2 further illustrates an embodiment of a tubular section of a catheter where the thickness of the side wall of the catheter body 120 is not even. The tubular section may be characterized as essentially eccentric annular, wherein the geometrical center of the lumen 200 is not collocated with the geometrical center of the outer surface of the side walls catheter body 120. Off center disposal of the lumen 200 may provide more room for the installation recess 125 within the side wall of the catheter body 120 by allowing the side wall to be thicker in one sector of the catheter body 120.

Figure 3:
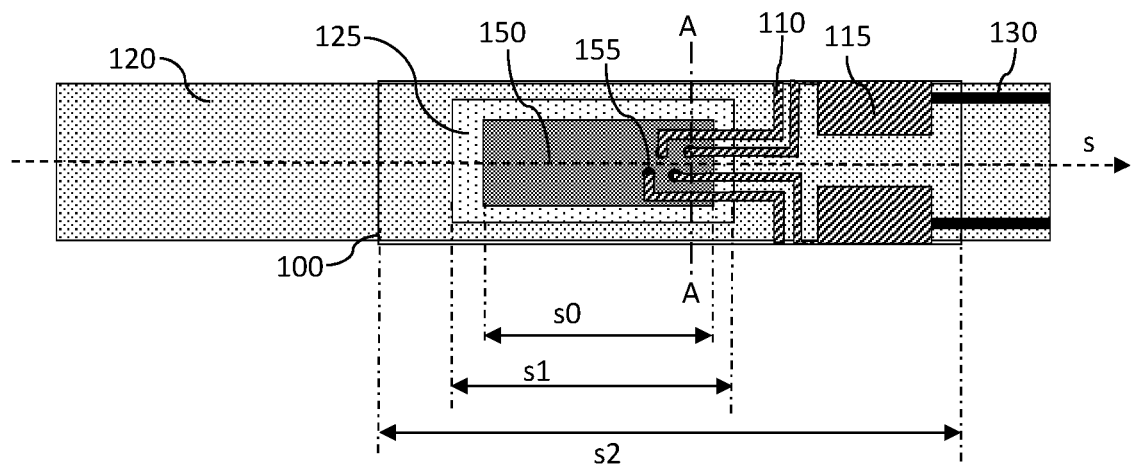
FIG. 3 illustrates a lateral, longitudinal view of a portion of a catheter portion according to a second embodiment.
Figure 4:
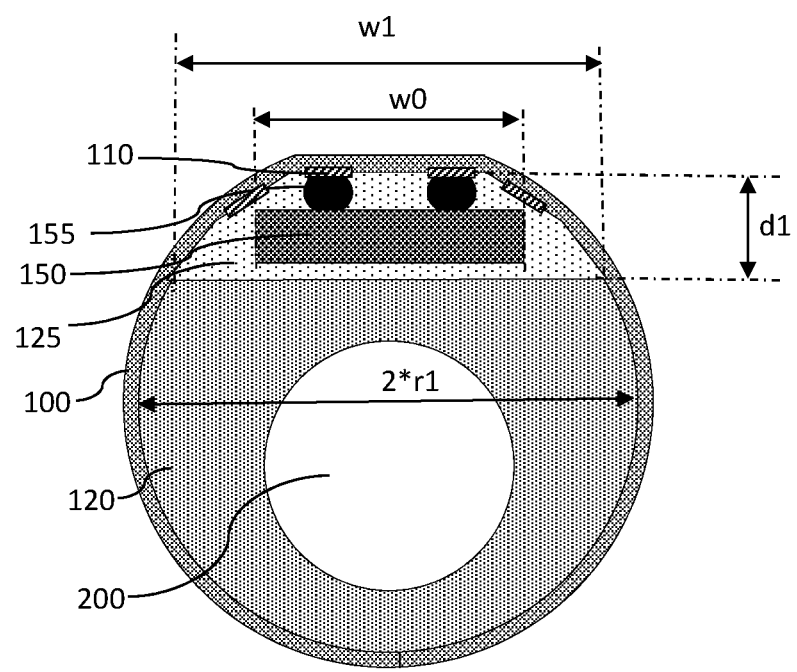
FIG. 4 illustrates a cross-section of a catheter.

FIGS. 3 and 4 illustrate a second exemplary embodiment. FIG. 3 illustrates a lateral, longitudinal view of a portion of a catheter portion. FIG. 4 illustrates a cross-section A-A of the catheter portion of the FIG. 3.

The assembly is in most aspects similar to that of FIGS. 1 and 2, but the installation recess 125 is now formed by removing material from the side wall of the catheter along a chord disposed on the outer surface of the side wall. This type of chordal installation recess 125 may be beneficial when the electronic device 150 is relatively wide, in other words when the ratio between the width w0 of the electronic device 150 and the diameter 2*r1 of the catheter is more than 0.4, that is the upper limit allowed for an electronic device in a quadrangle installation recess. The chordal installation recess 125 may allow installation of an electronic device 150 with a ratio up to 0.6 between the width w0 of the electronic device 150 and the diameter 2*r1 of the catheter. The chordal installation recess 125 of FIGS. 3 and 4 formed by removing a minor section from the side wall along a chord drawn on the outer surface of the side wall may thus allow installing a wider electronic device than the rectangular installation recess of FIGS. 1 and 2. Length s1 of the chordal installation recess 125 shall be greater than the length s0 of the electronic device 150, and less than the overall length s2 of the flexible circuit board 100. Preferably, the length s1 of the chordal installation recess 125 is less than the length s2 of the flexible circuit board. The width w1 of the installation recess 125 is now defined by the crossing points of the chord and the outer surface of the side wall of the catheter body 120. The depth d1 of a chordal installation recess 125 may be defined by height of the imaginary segment removed from the circular outer surface of the catheter body 120.

In the second embodiment, the installation recess 125 is preferably filled with protective filling. The protective filling may be applied before or after the flexible circuit board 100 is wrapped around the catheter body 120. When the flexible circuit board 100 is wrapped around the catheter body 120, the otherwise essentially circular cross-section of the wrapped flexible circuit board has a section at the location of the electronic device 150 defined by a chord. While this section extends along the longitudinal axis of the catheter body 120, a flat portion is created on the outer face of the oblong tubular portion of the catheter with the installation recess 125. The flat portion of the wrapped flexible circuit board 100 facilitates stability of the coupling between the contacts 155 of the electronic device 150 and the wiring 110 on the flexible circuit board. The flat portion may extend in the longitudinal direction over the entire length of the installation recess 125, or it may only appear only in the immediate vicinity of the solder bumps 155.

FIGS. 5a to 5d illustrate a lateral, longitudinal view of a portion of a catheter according to a third embodiment. In this embodiment, a single, oblong installation recess 125 is configured to house two electronic devices 150.

Figure 5A:
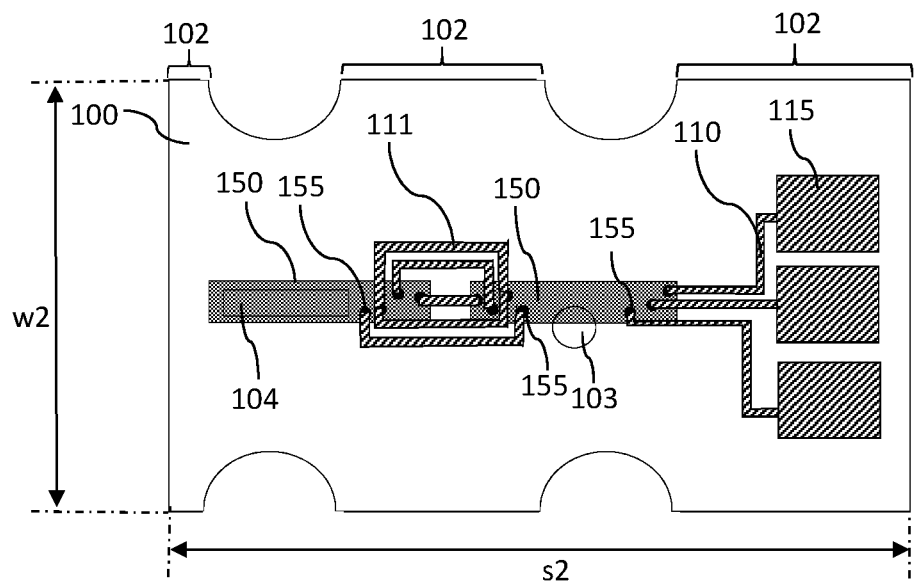
FIGS. 5a to 5d illustrate a catheter assembly according to a third embodiment.
Figure 5B:
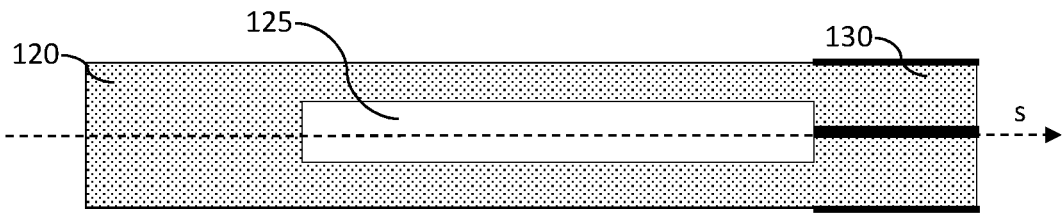
Figure 5C:
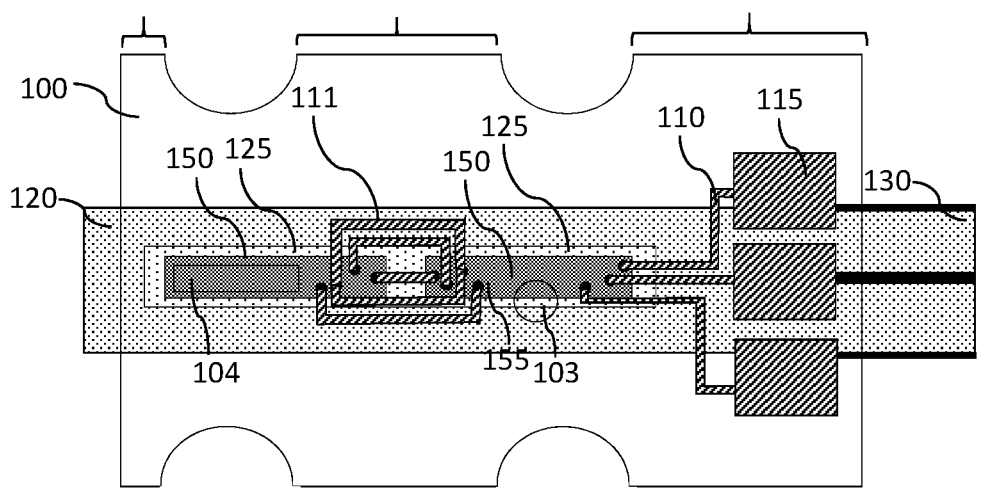

FIGS. 5a and 5c also illustrate a variation in which the flexible circuit board 100 is not configured to encircle the catheter body 120 over the flexible circuit board's entire length s2, but the flexible circuit board 100 comprises predefined portions 102 at which the width w2 of the flexible circuit board 100 is large enough to enable it to fully encircle the catheter. In other portions, the flexible circuit board 100 width is less than w2, so that the flexible circuit board 100 may only partially encircle the catheter body 120 on which the flexible circuit board 100 is wrapped. In other words, only predefined portions of the flexible circuit board 100 having the width w2 are wide enough to encircle the entire catheter body 120, but the portions with a width less than w2 do not encircle the catheter body 120 entirely, but only partially when wrapped. The predefined portions 102 that do not fully encircle the catheter may help retaining higher flexibility of the catheter and preventing buckling of the wrapped flexible circuit board when the catheter is bent.

This variation further illustrates one example on enabling application of the protecting filling into the recess. One or more holes 103 may be created in the flexible circuit board 100. These one or more holes 103 are disposed at a position that is at least partially collocated with an underlying installation recess 125, when the flexible circuit board 100 is wrapped around the catheter body 120. The holes 103 thus enable application of the protective filling into the installation recess 125 configured to protect the electronic device from contact with for example bodily fluids when in use and evacuation of air from the installation recess during application of the protective filling.

This variation further illustrates one example on allowing free thermal expansion of the protective filling disposed in the installation recess 125 on the electronic device 150. An elongated cut-out 104 may be created into the flexible circuit board 100, which is aligned with the location of the electronic device 150 and preferably smaller in dimensions that the electronic device 150. This cut-out 104 allows the protective filling covering the electronic device 150 to expand and contract during temperature changes without forcing the protective filling to flow horizontally and without changing the pressure of the filling in the installation recess 125. Such cut-out may be very useful when the electronic device 150 is a pressure sensor. The flexibility of the flexible circuit board may not be sufficient to allow the protective filling to expand or contract without causing a pressure change in the protective filling disposed in the installation recess with the pressure sensor. If the internal pressure of the protective filling changes, the expansion or contraction of the protective filling may cause a pressure measurement error. If the electronic device 150 is a pressure sensor with a pressure sensitive membrane or a diaphragm, the elongated cut-out 104 may be aligned with the location of the pressure sensing membrane or diaphragm and have the same dimensions as the membrane or diaphragm or it can be slightly smaller than the membrane or diaphragm.

As understood by a skilled person, the variations disclosed in the FIGS. 5a to 5c may be applied with any of the embodiments disclosed in this application.

The flexible circuit board 100 comprises further wiring 111 configured to provide interconnections between the two electronic devices 150. Wiring 111 may comprise a plurality of wires. More particularly, wiring 111 is connected between contacts 155 on the two electronic devices 150. Similar to wiring 110, the wiring 111 may carry any one of electrical power and signals. For example, one of the electronic circuits 150 may be a sensor device, and the other one may be an interface device. The signals provided by the sensor device may be input in the interface device, which may process the signals from the sensor device and feed the processed signals into the electrical wiring 130. The interface device may for example be configured to perform at least analog-to-digital conversion for one or more analog detection signals provided by the sensor device and to feed one or more digital signals towards external equipment at the proximal end of the catheter via one or more wires of the electrical wiring.

Disposing two electronic devices 150 within a single installation recess 125 enables disposing the two electronic devices 150 near to each other, and facilitates short interconnections between the electronic devices 150. A short interconnection is beneficial for example when a signal carried between the two electronic devices 150 is a sensitive, small analog signal. On the other hand, two separate recesses may have less effect on the flexibility of the catheter, and also the volume of the protective filling material may be smaller.

In a further embodiment, even more that two electronic devices 150 may be interconnected to each other with a single flexible circuit board 100. For example, one interface device may be coupled to two or more sensor devices so that a single interface device may serve two or more sensor devices disposed along the catheter.

Figure 5D:
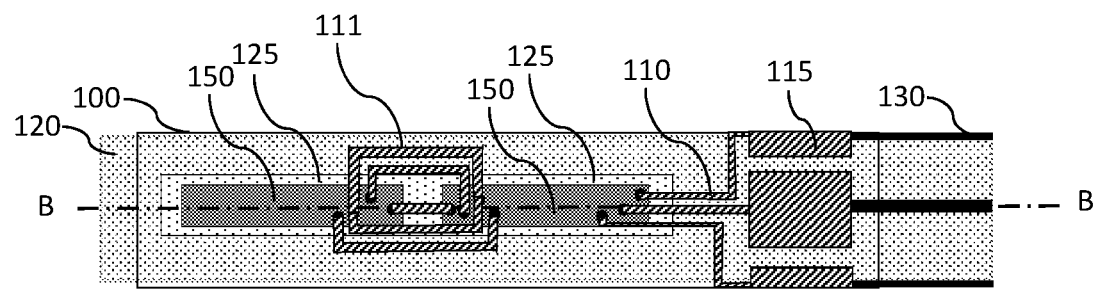
Figure 6:
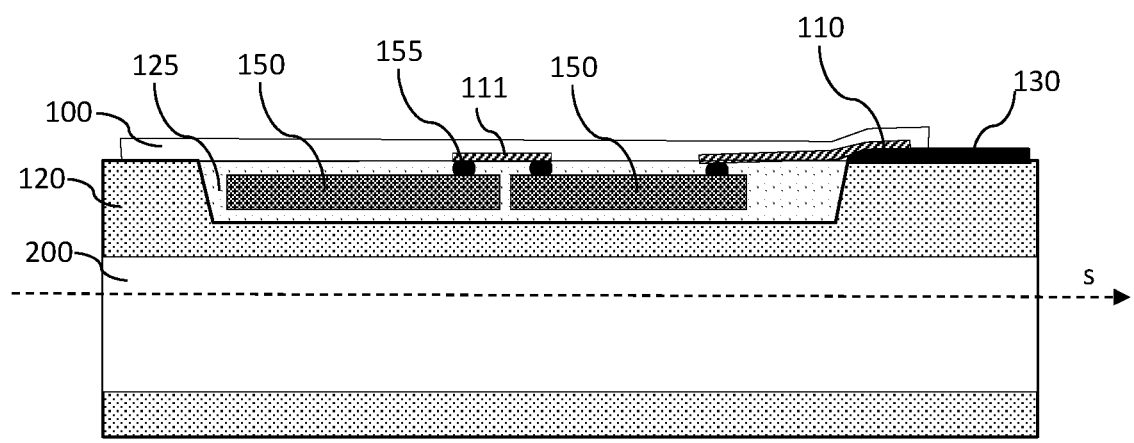
FIG. 6 illustrates a schematic view of a longitudinal cross-section a portion of a catheter.
Figure 7A:
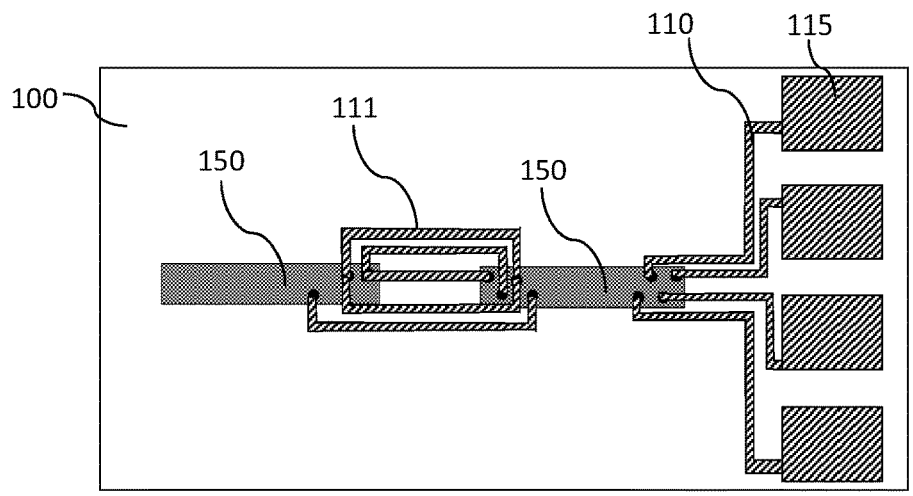
FIGS. 7a to 7d illustrate a fourth exemplary embodiment.
Figure 7B:
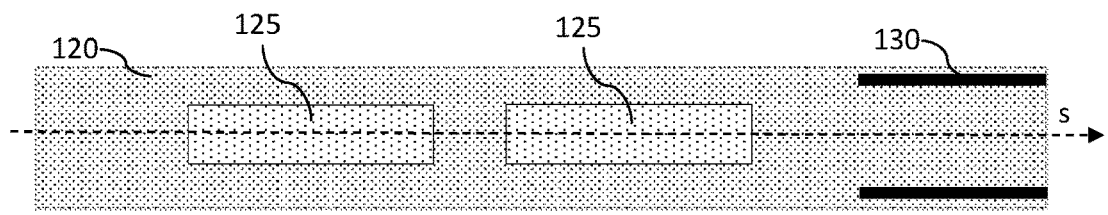
Figure 7C:
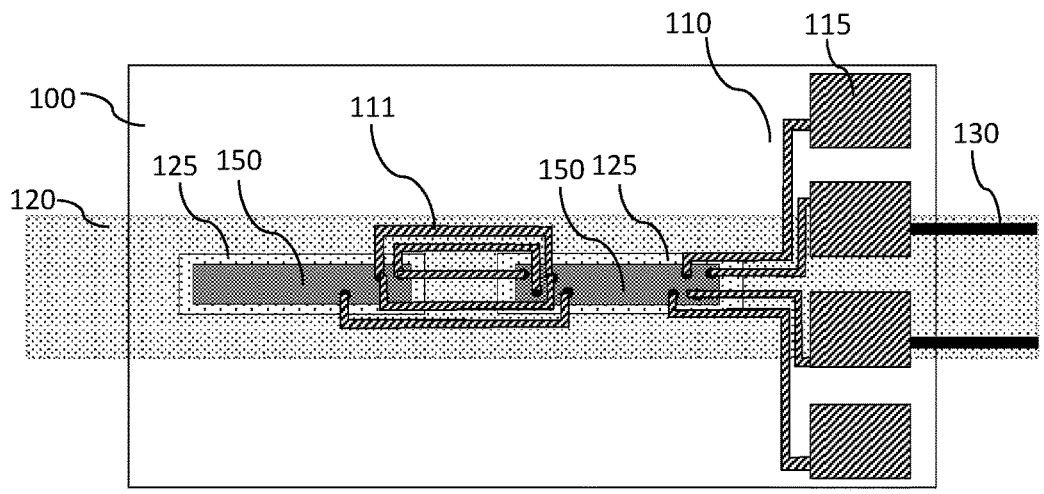
Figure 7D:
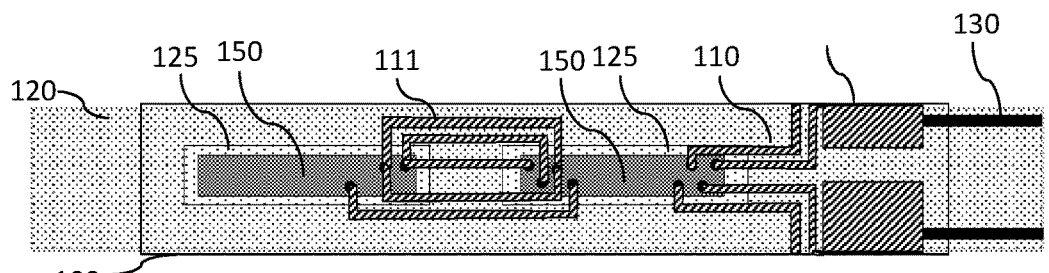

The FIG. 6 illustrates a schematic view of a longitudinal cross-section B-B of the portion of a catheter of the FIG. 5d. The flexible circuit board 100 extends longitudinally over the installation recess 125 filled with protective filling. Additional wiring 111 interconnects defined contacts 155 of the two electronic devices 150. This cross-section also shows how one of the coupling pads 115 makes a contact with the electrical wiring 130 disposed on the outer surface of the catheter body 120. This cross-section also illustrates that the sides of the installation recess 125 may be tilted, so that the cross-section of the installation recess becomes a trapezoid.

FIGS. 7a to 7d illustrate a fourth exemplary embodiment. In this embodiment, two separate oblong installation recesses 125 are disposed successively in the longitudinal direction of the catheter body 120. Each installation recess 125 is configured to house one electronic device 150. The two electronic devices 150 are connected to each other with wiring 111 disposed on the flexible circuit board 100 similarly to that in the third embodiment, except that the wiring 111 now extends between two separate installation recesses 125.

Figure 8:
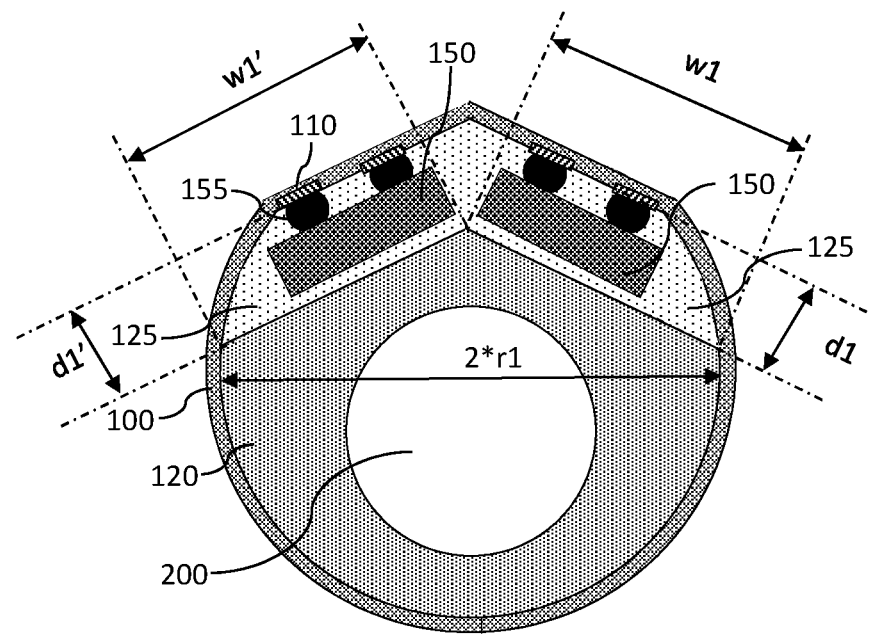
FIG. 8 illustrates a cross-section of a fifth exemplary embodiment.

The FIG. 8 illustrates a cross-section of a catheter according to fifth exemplary embodiment. In this embodiment, two electronic devices 150 are disposed side by side. Similar to the first and second embodiment, the lumen 200 is not disposed at the geometrical center of the catheter body 120. Such eccentric disposal of the lumen 200 facilitates increased volume of the catheter body 120 in one sector, enabling creating the two radially adjacent, interconnected installation recesses 125 with widths w1 and w1', which installation recesses 125 in this embodiment are located radially side by side but at different angle, thus covering two adjacent sectors of the catheter body 120. The widths w1, w1' of the two adjacent installation recesses 125 may be equal or different. The depths d1, d1' of the installation recesses 125 may also be equal of different.

The cross-section of the outer surface of the catheter body 120 in this embodiment has two adjacent linear sections defined by two chords crossing each other. Likewise, the cross-section of the catheter with the wrapped flexible circuit board 100 now has two adjacent linear sections defined by two chords. The flat sections are disposed at least at the location of the coupling 155 of the electronic devices with the wiring 110 of the flexible circuit board 100. In the embodiment illustrated in the FIG. 8, the joint between the two linear sections is drawn as an obtuse angle. Instead of such distinct, obtuse angle, the joint between the two adjacent flat areas may also be rounded.

Figure 9:
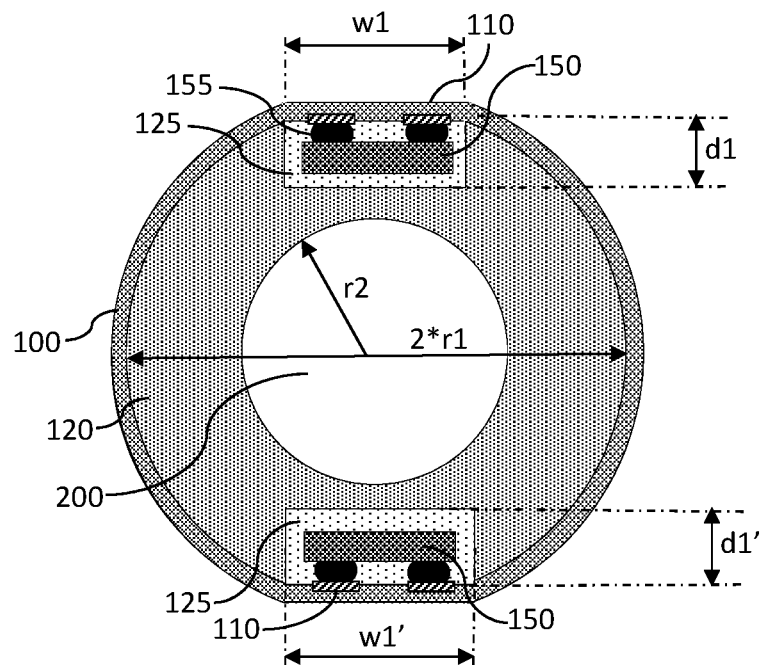
FIG. 9 illustrates a cross-section of a sixth exemplary embodiment

The FIG. 9 discloses a cross-section of a catheter according to sixth exemplary embodiment. In this embodiment, the lumen 200 is disposed at the center of the catheter body 120. There are two electronic devices 150 disposed at the same cross-section within two quadrangle installation recesses 125 disposed on opposite sides of the catheter body 120. Each electronic device 150 is coupled to the flexible circuit board 100 in the similar manner to the electronic device 150 of the first embodiment. The flexible wiring board 100 may have wiring to couple the two electronic devices to electrical wiring disposed on the surface of the catheter body 120 and/or wiring interconnecting at least some contacts 155 of the two electronic devices 150.

The widths w1, w1' of the installation recesses 125 may be equal or different. The depths d1 and d1' of the installation recesses 125 may also be equal or different, as long as each installation recess 125 conforms with the limitation of depth defined by thickness of the side wall of the catheter body 120.

The catheter body may have sections with different cross-section. The embodiments described above are preferably implemented in a section of the catheter body which is tubular, in other words which comprises a lumen within the catheter body. Some catheters have a hollow lumen which traverses essentially throughout the entire length of the catheter, which length may be for example 180 cm. In some catheters, such as the earlier mentioned rapid exchange catheters, a lumen configured for insertion of a guide wire is disposed only at the distal portion of the catheter.

A catheter may have a plurality of electronic devices or pairs of electronic devices disposed at different distances from the distal end of the catheter. Each electronic device, a pair of electronic devices or a plurality of electronic devices may be assembled using any one of the above described embodiments, a combination thereof and a combination of individual features varying between the embodiments, and the catheter may therefore comprise a single or a plurality of flat areas caused by one or more installation recesses.

The wrapping of the flexible circuit board around the catheter body is preferably ensured with some suitable method to hold the flexible circuit board firmly in place. For example, an adhesive, heat shrinkable tubing may be disposed around the catheter, thus confirming the outer periphery of the catheter. The tubing may be disposed so that it covers the portion of the catheter with the flexible circuit board. Preferably, the tubing extends longitudinally beyond both the distal and the proximal end of the wrapped flexible circuit board. The tubing may also extend over a longer portion of the catheter, for example covering multiple sets of electronic devices disposed at different locations along the catheter body.

The flexible circuit board may comprise one or more holes or openings. The holes or openings in the flexible circuit board may be disposed at least partially in the area of the underlying installation recess. The holes or openings in the flexible circuit board may be utilized for purposes like applying protective filling, evacuating air when applying the protective filling, and allowing free thermal expansion of the protective filling without increasing the internal pressure of the protective filling. The flexible circuit board may not extend around the periphery of the catheter body over the flexible circuit board's entire length, but the flexible circuit board may be configured to extend around the periphery of the catheter body only at selected fixing locations and where contacts to the electrical wiring are required on all sides of the catheter body.

It is apparent to a person skilled in the art that as technology advanced, the basic idea of the invention can be implemented in various ways. The invention and its embodiments are therefore not restricted to the above examples, but they may vary within the scope of the claims.

The invention claimed is:

1. An elongated catheter comprising a tubular section with a side wall with essentially annular cross-section defined by an outer surface and an inner surface of the tubular section, the catheter comprising:
   at least one longitudinal installation recess in the outer surface of the tubular section;
   a flexible circuit board wrapped around the outer surface of the tubular section and covering at least a majority of the at least one longitudinal installation recess on the outer surface of the tubular section by the flexible circuit board;
   electrical wiring disposed on the outer surface of the tubular section; and
   at least one electronic device assembled on the flexible circuit board wrapped around the tubular section so that the at least one electronic device is disposed within the at least one longitudinal installation recess under the flexible circuit board;
   wherein the at least one electronic device is interconnected via the flexible circuit board with the electrical wiring.

2. The elongated catheter according to claim 1, wherein the catheter further comprises:
   the at least one electronic device comprises at least one first electronic device and at least one second electronic device,
   wherein the at least one first electronic device and the at least one second electronic device are assembled on the flexible circuit board and disposed within at least one longitudinal installation recess,
   and wherein the at least one first electronic device is interconnected via the flexible circuit board with the electrical wiring and the at least one second electronic device is interconnected via the flexible circuit board with the first electronic device.

3. The elongated catheter according to claim 1, wherein at least predefined portions of the flexible circuit board wrapped on the tubular section essentially encircle the tubular section of the catheter.

4. The elongated catheter according to claim 1, wherein the at least one installation recess extends a first predefined distance over the longitudinal dimension of the catheter, the flexible circuit board extends a second predefined distance along the longitudinal dimension of the catheter, wherein the second predefined distance is greater than the first predefined distance.

5. The elongated catheter according to claim 1, wherein an essentially circular cross-section of the wrapped flexible circuit board comprises one or more essentially circular segments and at least one chordal segment at the portion of the cross-section of the wrapped flexible circuit board at which the at least one electronic device is assembled on the flexible circuit board.

6. The elongated catheter according to claim 1, wherein the depth of the at least one installation recess is less than the distance between the outer surface and the inner surface of the tubular section, but more than the height of the at least one electronic device within the installation recess.

7. The elongated catheter according to claim 1, wherein the cross section of the at least one installation recess is any one of a quadrangle crossing the outer surface of the tubular section so that two opposite sides of the quadrangle cross the outer surface of the tubular section, and a minor chordal segment removed from the outer surface of the tubular section.

8. The elongated catheter according to claim 1, wherein the at least one electronic device is of flip chip type.

9. The elongated catheter according to claim 1, wherein a wrapping layer configured to hold the flexible circuit board in place and to confirm the outer periphery of the catheter is disposed around the catheter at least over the second distance along the longitudinal dimension of the catheter.

10. The elongated catheter according to claim 9, wherein the wrapping layer comprises adhesive heat shrinkable tubing.

11. The elongated catheter according to claim 1, wherein the electrical wiring disposed on the outer surface of the tubular section is configured to lead at least one of electrical power and a control signal into at least one of the electronic devices and to lead electrical signals out of at least one of the electronic devices.

12. The elongated catheter according to claim 1, wherein a protective filling is applied into the installation recess in which the at least one electronic device is disposed, the protective filling configured to surround the at least one electronic device on all sides and to prevent direct contact of bodily fluids with the at least one electronic device.

13. The elongated catheter according to claim 1, wherein the flexible circuit board further comprises at least one hole at least partially collocated with the installation recess, the at least one hole configured to enable application of protective filling into the installation recess or to enable evacuation of air from the installation recess during application of the protective filling.

14. The elongated catheter according to claim 1, wherein the flexible circuit board further comprises at least one elongated cut-out collocated with at least one electronic device, wherein the at least one elongated cut-out is configured to prevent changes in the internal pressure of the protective filling within the underlying installation recess due to temperature changes by allowing the protective filling to expand and contract.

15. A method for manufacturing an elongated catheter comprising a tubular section with a side wall with essentially annular cross-section defined by an outer surface and an inner surface of the tubular section, the method comprising:
   assembling at least one electronic device on a flexible circuit board;
   wrapping the flexible circuit board around the outer surface of the tubular section of the catheter, so that the flexible circuit board covers at least a majority of at least one longitudinal installation recess on the outer surface of the tubular section and the at least one electronic device assembled on the flexible circuit board that is being wrapped around the tubular section becomes disposed within the at least one longitudinal installation recess in the outer surface of the tubular section under the flexible circuit board; and interconnecting the at least one electronic device with electrical wiring disposed on the outer surface of the tubular section via the flexible circuit board.

16. The method according to claim 15, wherein the at least one electronic device comprises at least one first electronic device and at least one second electronic device, and the method comprises:

assembling the at least one first electronic device and the at least one second electronic device are assembled on the flexible circuit board and disposed within at least one longitudinal installation recess, interconnecting the at least one first electronic device via the flexible circuit board with the electrical wiring, and interconnecting the at least one second electronic device via the flexible circuit board with the first electronic device.

17. The method according to claim 15, wherein the wrapping causes at least predefined portions of the flexible circuit board to essentially encircle the tubular section of the catheter.

18. The method according to claim 15, wherein the at least one installation recess extends a first predefined distance over the longitudinal dimension of the catheter, the flexible circuit board extends a second predefined distance along the longitudinal dimension of the catheter, wherein the second predefined distance is greater than the first predefined distance.

19. The method according to claim 15, wherein the method further comprises:

disposing a wrapping layer configured to hold the flexible circuit board in place and to confirm the outer periphery of the catheter around the catheter at least over a second distance along the longitudinal dimension of the catheter.

20. The method according to claim 15, further comprising:

applying a protective filling into the installation recess in which the at least one electronic device is disposed, wherein the protective filling is configured to surround the at least one electronic device on all sides and to prevent direct contact of bodily fluids with the at least one electronic device.

21. A method according to claim 15, wherein the method further comprises:

manufacturing in the flexible circuit board at least one hole configured to be at least partially collocated with the installation recess, the at least one hole configured to enable application of protective filling into the installation recess or to enable evacuation of air from the installation recess during application of the protective filling.

22. The method according to claim 15, wherein the method further comprises:

manufacturing in the flexible circuit board at least one elongated cut-out configured to be collocated with at least one electronic device, wherein the at least one elongated cut-out is configured to prevent changes in the internal pressure of the protective filling within the underlying installation recess due to temperature changes by allowing the protective filling to expand and contract.

\* \* \* \* \*